(12) United States Patent
Caldwell et al.

(10) Patent No.: US 7,825,067 B1
(45) Date of Patent: Nov. 2, 2010

(54) PERFORATED LANDSCAPING FILM WITH DISCRETELY APPLIED WEED CONTROL AGENT

(75) Inventors: E. Neal Caldwell, Knoxville, TN (US); Robert Nytko, Knoxville, TN (US)

(73) Assignee: Dalen Products, Inc., Knoxville, TN (US)

( * ) Notice: Subject to any disclaimer, the term of this patent is extended or adjusted under 35 U.S.C. 154(b) by 676 days.

(21) Appl. No.: 11/029,273

(22) Filed: Jan. 5, 2005

(51) Int. Cl.
*A01N 25/34* (2006.01)
*A01N 25/08* (2006.01)
*A01N 25/24* (2006.01)
*A01G 13/02* (2006.01)

(52) U.S. Cl. ............... 504/116.1; 47/9; 47/31.1; 514/499; 504/358; 504/360

(58) Field of Classification Search ............ 504/116, 504/358, 360; 47/9, 25, 56, 95; 111/102, 111/199, 230, 900; 514/499
See application file for complete search history.

(56) References Cited

U.S. PATENT DOCUMENTS

| | | | |
|---|---|---|---|
| 2,202,664 A | 5/1940 | Leatherman | |
| 3,384,993 A | 5/1968 | Kane | |
| 3,592,792 A | 7/1971 | Newland et al. | |
| 3,891,423 A | 6/1975 | Stanley et al. | |
| 3,939,606 A | 2/1976 | Vandemark et al. | |
| 4,243,703 A | 1/1981 | Palvarini et al. | |
| 4,350,678 A | 9/1982 | Palvarini et al. | |
| 4,881,344 A | 11/1989 | Frey et al. | |
| 5,139,566 A | 8/1992 | Zimmerman | |
| 5,181,952 A | 1/1993 | Burton et al. | |
| 5,575,112 A | 11/1996 | Scheubel | |
| 5,644,998 A * | 7/1997 | Krolick | 111/102 |
| 5,873,194 A | 2/1999 | Caldwell | |
| 6,114,431 A | 9/2000 | Lee et al. | |
| 6,324,781 B1 * | 12/2001 | Stevens | 47/9 |
| 6,329,032 B1 | 12/2001 | Lee et al. | |
| 6,429,156 B1 * | 8/2002 | Tipler et al. | 442/123 |
| 6,593,276 B2 | 7/2003 | Walley et al. | |

FOREIGN PATENT DOCUMENTS

EP 0 362 701 4/1990

* cited by examiner

*Primary Examiner*—John Pak
*Assistant Examiner*—Andriae M Holt
(74) *Attorney, Agent, or Firm*—Luedeka, Neely & Graham, PC

(57) ABSTRACT

A landscaping film, including a film sheet having a plurality of perforations defined therethough and discrete deposits of a weed control agent at locations on the film corresponding to the locations of the perforations.

18 Claims, 3 Drawing Sheets

PERFORATED LANDSCAPING FILM WITH DISCRETELY APPLIED WEED CONTROL AGENT

FIELD OF THE INVENTION

This invention relates generally to landscaping films. More particularly, this invention relates to perforated landscaping films incorporating a weed control agent such as copper hydroxide.

BACKGROUND AND SUMMARY OF THE INVENTION

Landscaping film and fabrics incorporating weed control agents are known. However, such films have various disadvantages and are expensive or complicated to produce. The invention overcomes disadvantages associated with conventional films and enables significantly decreased production costs.

With regard to the foregoing, the present invention is directed to a perforated landscaping film, including a film sheet having a plurality of perforations defined therethough and discrete deposits of a weed control agent at locations on the film corresponding to the locations of the perforations.

In a preferred embodiment, the film sheet is a polymer film having the weed or root control agent supplied to discrete locations of only one surface thereof. Although it has been observed that the weed control agent as applied to discrete locations of only one surface of the film will accomplish good root penetration control, it is preferred, in another embodiment, that the weed control agent be supplied to discrete locations on both surfaces of the film.

The root or weed control agent is preferably a copper containing compound, such as copper hydroxide. The weed control agent is preferably applied by a printing process, either before or after the perforations are formed. Alternatively, the weed control agent may be applied by coating the needles used to perforate the film.

Landscaping films in accordance with the invention advantageously enable improved performance in a cost effective manner.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
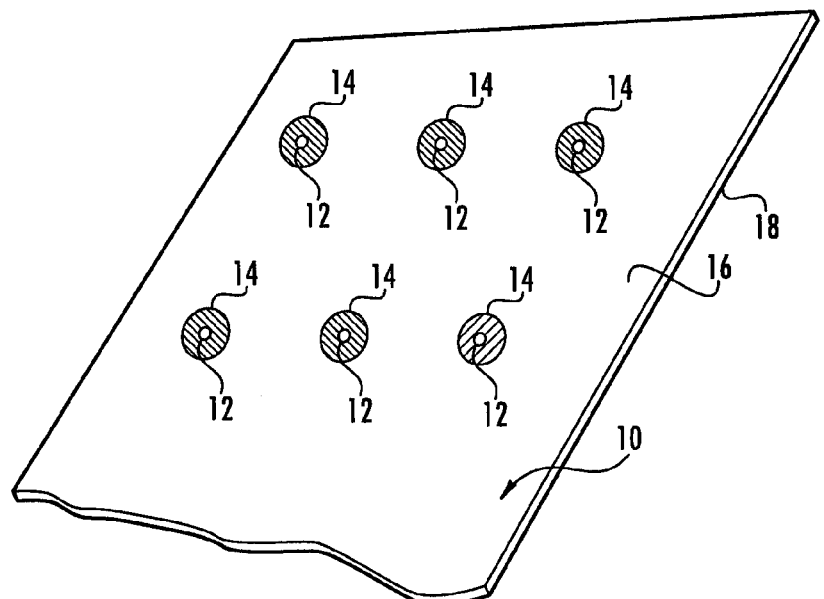
FIG. 1 is a detailed perspective view of a portion of a landscaping film provided in accordance with a preferred embodiment of the invention.

With initial reference to FIG. 1, the invention relates to a weed-growth inhibiting landscaping film 10 having a plurality of perforations 12 and including a plurality of discrete deposits of a root or weed control agent 14 at locations on the film 10 substantially corresponding to the locations of the perforations 12. As used herein, the term "weed control agent" will be understood to refer to agents suitable for inhibiting or retarding root, weed, or other plant growth.

The film 10 is preferably made using as a starting material a polymer film 15 having a surface 16 and an opposite surface 18. For example, the film 15 may be a polyethylene film of a type commonly used as a landscaping film, and preferably having a thickness of between about 0.5 mils and about 3.0 mils and containing a black or brown pigment.

The perforations 12 are preferably provided in a predetermined pattern so as to be uniformly spaced and distributed and formed as by needle-punching or laser burning through the film 15 from the surface 18. For example, perforations having a diameter of from about 0.01 to about 0.025 inches and spaced about 3/8 inch on center in two directions.

The deposits of the weed control agent 14 are at locations substantially corresponding to the locations of the perforations 12 and may be applied to portions of the surface 16 or the surface 18 or both. In a preferred embodiment, the deposits of weed control agent 14 may be supplied as by printing the deposits of the agent 14 as dots having a diameter of from about 0.062 to about 0.125 inches. In this regard, it is preferred to render the dots of the agent 14 as small as practical within the ability of the mechanisms to synchronize the relative positions of the printed dots and the needle punched apertures. The printing may be performed with liquid or solid weed control agents in the same manner as liquid and solid inks are used in printing processes.

The deposits of the weed control agent 14 are preferably deposits of a substantially water insoluble copper compound selected from the group consisting of copper oxychloride, copper oxide, copper carbonate and, most preferably, copper hydroxide. Suitable copper compounds are available in powder form under the tradenames KOCIDE and SPIN OUT from Griffin, LLC of Valdosta, Ga. The powder form of the copper compound is preferably dispersed within an aqueous solution incorporating a binder and applied to desired locations on film 15. However, it will be understood that the weed control agent 14 may be of other composition configured to inhibit weed or other plant growth and to adhere to the film 15.

Figure 2:
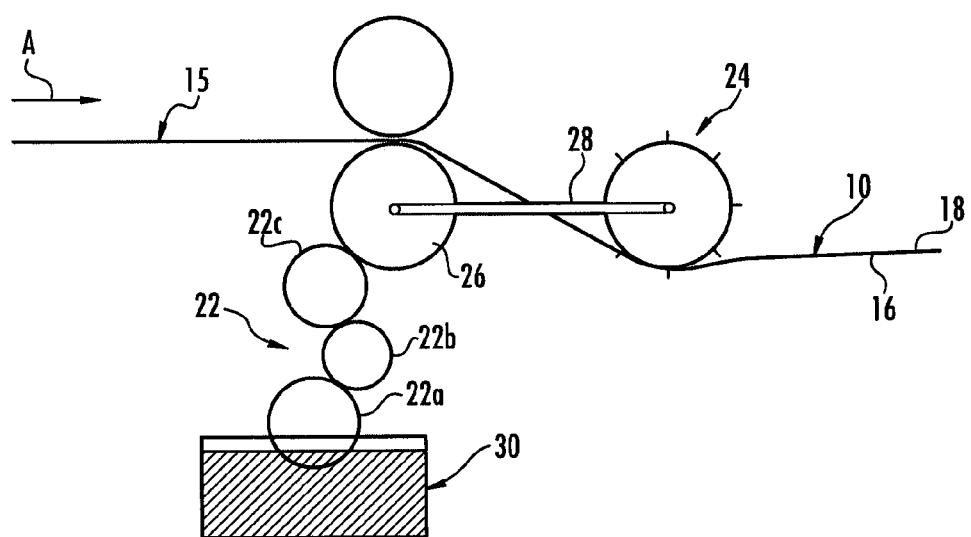
FIG. 2 is a schematic diagram of a preferred process for making the film of FIG. 1.

With reference to FIG. 2, there is shown a schematic diagram of a preferred process 20 for making the film 10. The film 15 is fed in the direction of arrow A past a flexographic or offset tower 22 for depositing, as by printing, the deposits of the weed control agent 14 onto desired locations of the film 15. The thus treated film 15 is then fed through a perforating roller 24 for forming the perforations 12 to yield the film 10. Alternatively, the sequence may be reversed, with the perforating roller 24 located before the flexographic tower 22.

To enable the deposits of the weed control agent 14 at the locations of the perforations 12, a print roller 26 of the tower 22 and the perforating roller 24 are synchronized or registered, as by a connector 28. In this regard, it will be understood that the print roller 26 is preferably configured so as to print the weed control agent 14, supplied to the print roller 26 via a supply 30 and rollers 22a-c, in a pattern corresponding to the configuration of the perforations 12 as formed by the perforating roller 24. Thus, discrete deposits of the weed control agent 14 are applied at locations on the film 15 to correspond to the locations of the perforations 12 to yield the desired landscaping film 10. The print roller 26 is preferably configured so as to apply the weed control agent 14 as dots or discs having a diameter slightly greater than the dimensions of the perforations 12.

The landscaping film 10 advantageously provides a structure which inhibits weed or other undesired plant growth by providing both mechanical and chemical deterrents. For example, the film substrate inhibits growth of weed or other plant life therethough, yet enables both air and water to migrate there through via the perforations 12. In conventional perforated film, the sites of the perforations are sites which are susceptible to weed or other plant growth, since the mechanical barrier, i.e., the film, is absent.

The present invention advantageously provides a weed control agent at the locations of the perforations so as to provide a chemical deterrent to weed or other plant growth at the perforation sites. In addition, the invention enables significant reduction in the cost associated with providing a film having both mechanical and chemical deterrent properties.

By providing a perforated film having weed control agent only at the perforation sites, the present invention effectively provides desired chemical inhibition of weed or root growth at the locations where plant growth is most likely to appear, while minimizing the amount of weed control agent that is used. This advantageously enables a landscaping film having enhanced performance features while avoiding many of the cost disadvantages associated with other landscaping films.

Figure 3:
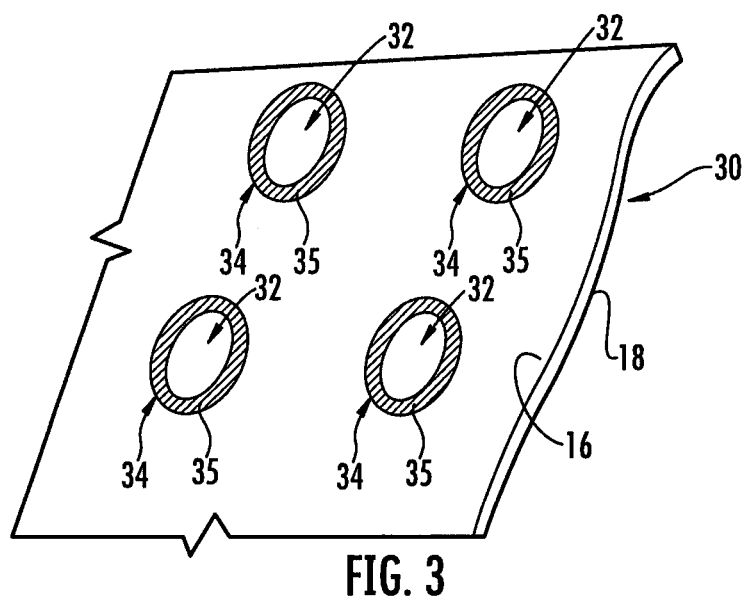
FIG. 3 is a perspective view of a portion of a landscaping film provided in accordance with an alternate embodiment of the invention.

With reference to FIG. 3, there is shown an alternate embodiment of a weed-growth inhibiting landscaping film 30 having a plurality of perforations 32 and including a plurality of discrete deposits of a weed control agent 34 at locations on the film 30 substantially corresponding to the locations of the perforations 32. As will be observed, the deposits of the weed control agent 34 are provided as annular rings 35 at the locations of the perforations 32. The locations of the perforations 32 preferably correspond to the locations of the perforations 14 described previously.

Figure 4:
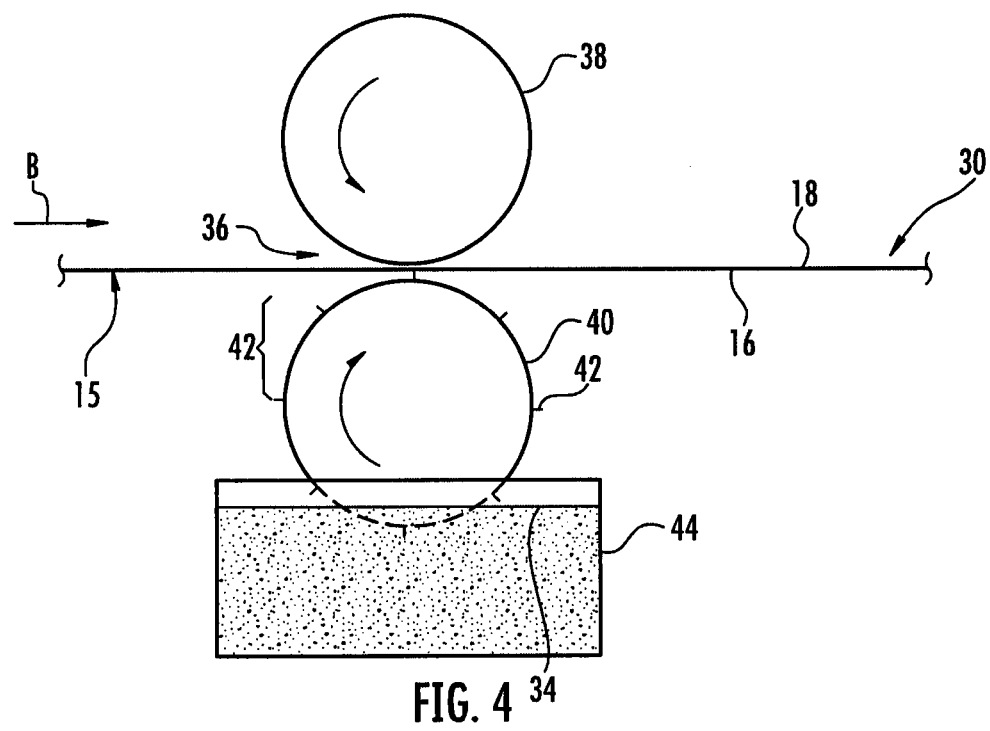
FIG. 4 is a schematic diagram of a preferred process for making the film of FIG. 3.

The film 30 may be made using a polymer film such as the previously described film 15 having opposite surfaces 16 and 18. In this regard, and with reference to FIG. 4, the film 30 may be made by traveling the film 15 in the direction of arrow B through a nip 36 defined between a backup roller 38 and a perforating roller 40 having a plurality of perforating needles 42.

The roller 40 extends into a supply 44 of the weed control agent 34, such that the tips of the perforating needles 42 are coated with the weed control agent 34. As each of the needles 42 perforates the film 15, the weed control agent 34 is deposited in the form of the annular rings 35 on the surface 16 surrounding each perforation of the film 15 at the locations of the perforations 32 to yield the landscaping film 30. The weed control agent 34 preferably corresponds to the weed control agent 14 described previously.

Figure 5:
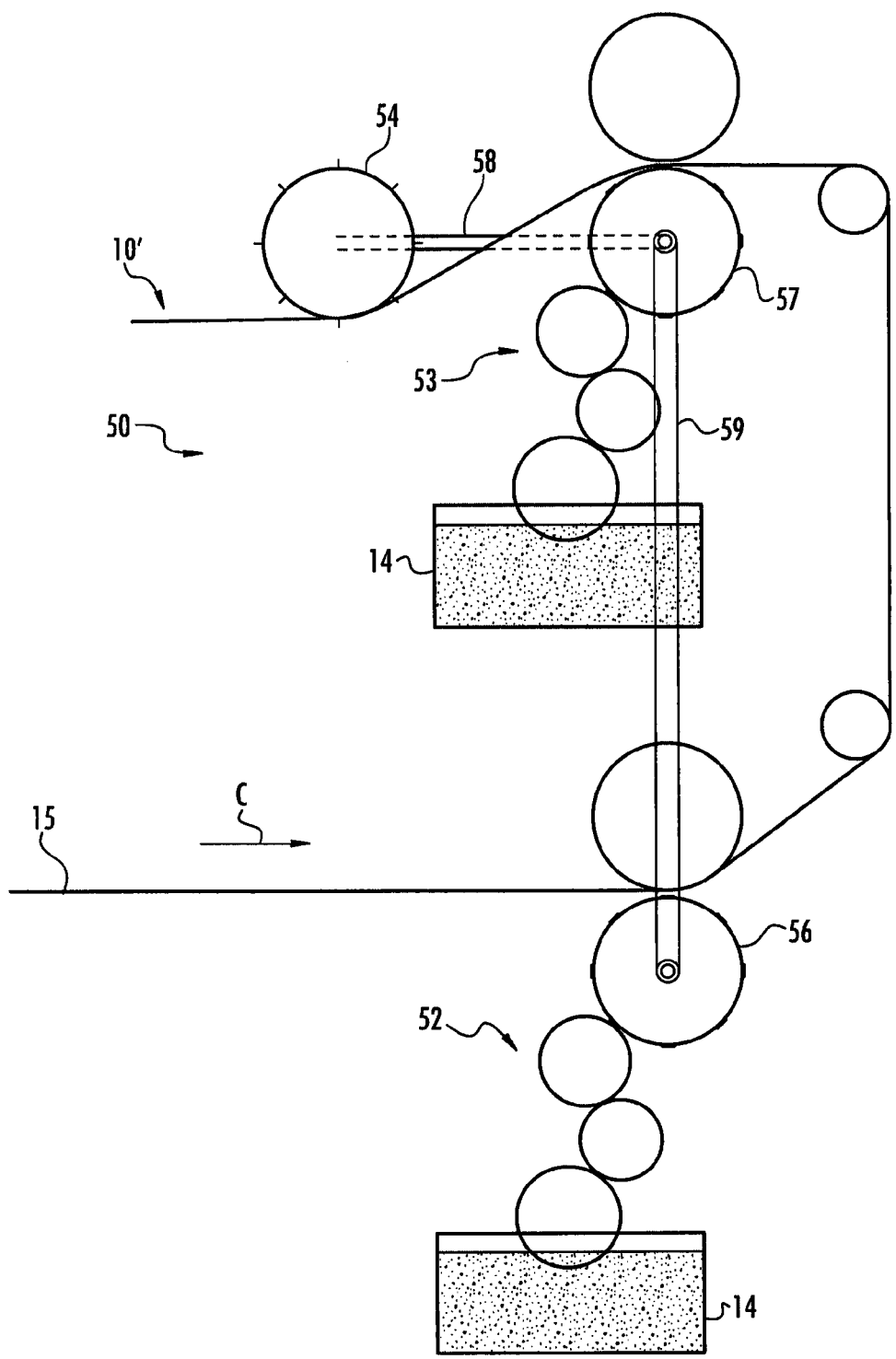
FIG. 5 is a schematic diagram showing an alternate process for making film.

With reference now to FIG. 5, there is shown a schematic diagram of a preferred process 50 for making a film 10'. The film 10' is identical to the film 10, except that it has the weed control agent applied to corresponding discrete locations on both sides of the film. The film 15 is fed in the direction of arrow C past first and second flexographic or offset towers 52 and 53 for depositing, as by printing, the deposits of the weed control agent 14 onto desired locations on both sides of the film 15. The thus treated film 15 is then fed through a perforating roller 54 for forming the perforations 12 to yield the film 10. Alternatively, the sequence may be reversed, with the perforating roller 24 located before the flexographic tower 22.

To enable the deposits of the weed control agent 14 at the locations of the perforations, print rollers 56 and 57 of the towers 52 and 53, respectively, and the perforating roller 54 are synchronized or registered, as by a connector 58 between the roller 57 and the perforator 54, and a connector 59 synchronizing the rollers 56 and 57. The print rollers 56 and 57 are preferably configured so as to print the weed control agent 14 in a pattern corresponding to the configuration of the perforations as formed by the perforating roller 54. Thus, discrete deposits of the weed control agent 14 are applied at locations on both sides of the film 15 to correspond to the locations of the perforations to yield the desired landscaping film 10'. The print rollers 56 and 57 are preferably configured in the manner of the print roller 26 so as to apply the weed control agent 14 as dots or circles having a diameter slightly greater than the dimensions of the perforations.

The perforated landscaping film has both mechanical and chemical deterrents of undesired plant growth. The perforated landscaping film comprises a polymer film sheet to provide said mechanical deterrent, wherein the film sheet has a plurality of uniformly spaced and distributed perforations to enable water and air to migrate through the film, and discrete deposits of a weed control agent that are adhered to the film sheet and located only at the locations of the perforations to provide said chemical deterrent at the perforations to inhibit weed growth at the locations of the perforations, wherein (i) the discrete deposits are applied as dots, discs or annular rings surrounding each perforation of the film sheet, and (ii) each dot, disc or annular ring has a diameter slightly greater than the dimensions of the perforations. The perforated landscaping film can be prepared by the steps of providing a polymer film sheet which provides a mechanical barrier to plant growth, the film having opposite sides; forming a plurality of perforations throughout the film sheet at uniformly spaced and distributed locations to enable water and air to migrate through the film; and applying discrete deposits of a weed control agent only at said locations on at least one side of the film sheet to provide a chemical deterrent to plant growth at said locations, wherein (i) the discrete deposits are applied as dots, discs or annular rings surrounding each perforation of the film sheet, and (ii) each dot, disc or annular ring has a diameter slightly greater than the dimensions of the perforations.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A perforated landscaping film having both mechanical and chemical deterrents of undesired plant growth, comprising a polymer film sheet to provide said mechanical deterrent, wherein the film sheet has a plurality of uniformly spaced and distributed perforations to enable water and air to migrate through the film, and discrete deposits of a weed control agent that are adhered to the film sheet and located only at the locations of the perforations to provide said chemical deterrent at the perforations to inhibit weed growth at the locations of the perforations, wherein (i) the discrete deposits are applied as dots, discs or annular rings surrounding each perforation of the film sheet, and (ii) each dot, disc or annular ring has a diameter slightly greater than the dimensions of the perforations.

2. The film of claim 1, wherein the film comprises a polyethylene film.

3. The film of claim 1, wherein the weed control agent comprises a water insoluble copper compound.

4. The film of claim 1, wherein the weed control agent is supplied by printing the weed control agent onto a surface of the film only at the locations of the perforations.

5. The film of claim 4, wherein the perforations are provided by perforating the film after the weed control agent has been printed onto the surface of the film.

6. The film of claim 4, wherein the perforations are provided by perforating the film before the weed control agent has been printed onto the surface of the film.

7. The film of claim 1, wherein the weed control agent is supplied by coating perforating needles with the weed control agent and contacting the film with the perforating needles to provide the perforations and to deposit the weed control agent onto the film only at the locations of the perforations.

8. The film of claim 7, wherein the deposits of the weed control agent are provided as annular rings.

9. The film of claim 1, wherein the deposits of weed control agent are supplied to both sides of the film only at the locations of the perforations.

10. A method of making a perforated landscaping film, comprising the steps of:
providing a polymer film sheet which provides a mechanical barrier to plant growth, the film having opposite sides;
forming a plurality of perforations throughout the film sheet at uniformly spaced and distributed locations to enable water and air to migrate through the film; and
applying discrete deposits of a weed control agent only at said locations on at least one side of the film sheet to provide a chemical deterrent to plant growth at said locations, wherein (i) the discrete deposits are applied as dots, discs or annular rings surrounding each perforation of the film sheet, and (ii) each dot, disc or annular ring has a diameter slightly greater than the dimensions of the perforations.

11. The method of claim 10, wherein the weed control agent is supplied at the discrete locations on both sides of the film.

12. The method of claim 10, wherein the weed control agent is supplied prior to the step of forming the perforations.

13. The method of claim 10, wherein the weed control agent is supplied after the step of forming the perforations.

14. The method of claim 10, wherein the weed control agent is supplied only at the locations of the perforations as the perforations are formed.

15. The method of claim 10, wherein the weed control agent is supplied by printing the weed control agent at said locations.

16. The method of claim 10, wherein the weed control agent is supplied by printing the weed control agent at the discrete locations and the perforations are formed at said locations within the printed weed control agent.

17. The method of claim 10, wherein the weed control agent is supplied by printing the weed control agent at said locations in a liquid form.

18. The method of claim 10, wherein the weed control agent is supplied by printing the weed control agent at said locations in a solid form.

* * * * *